United States Patent
Jianning et al.

(10) Patent No.: US 11,141,464 B2
(45) Date of Patent: Oct. 12, 2021

(54) GLP-1 POLYPEPTIDE HAVING GLP-1 RECEPTOR AGONIST ACTIVITY AND USE THEREOF

(71) Applicant: Liu Jianning, Jiangsu (CN)

(72) Inventors: Liu Jianning, Jiangsu (CN); Wang Jingyi, Jiangsu (CN)

(73) Assignee: Liu Jianning, Jiangsu (CN)

( * ) Notice: Subject to any disclaimer, the term of this patent is extended or adjusted under 35 U.S.C. 154(b) by 0 days.

(21) Appl. No.: 16/240,324

(22) Filed: Jan. 4, 2019

(65) Prior Publication Data

US 2020/0215161 A1  Jul. 9, 2020

Related U.S. Application Data

(63) Continuation of application No. PCT/CN2018/112789, filed on Oct. 30, 2018.

(51) Int. Cl.

| | | |
|---|---|---|
| *A61K 38/26* | (2006.01) |
| *A61K 38/28* | (2006.01) |
| *C07K 5/00* | (2006.01) |
| *C07K 7/00* | (2006.01) |
| *C07K 16/00* | (2006.01) |
| *C07K 17/00* | (2006.01) |
| *A61P 3/10* | (2006.01) |
| *A61P 7/12* | (2006.01) |
| *C07K 14/605* | (2006.01) |
| *A61K 38/00* | (2006.01) |
| *A61P 3/04* | (2006.01) |
| *A61P 1/00* | (2006.01) |
| *A61P 9/10* | (2006.01) |

(52) U.S. Cl.
CPC ............ *A61K 38/26* (2013.01); *A61P 1/00* (2018.01); *A61P 3/04* (2018.01); *A61P 3/10* (2018.01); *A61P 9/10* (2018.01); *C07K 14/605* (2013.01)

(58) Field of Classification Search
None
See application file for complete search history.

(56) References Cited

U.S. PATENT DOCUMENTS

| | | | |
|---|---|---|---|
| 2006/0229248 A1 | 10/2006 | Knudsen et al. | |
| 2010/0009904 A1 | 1/2010 | Lv et al. | |
| 2017/0281788 A1* | 10/2017 | Dimarchi | C07K 14/605 |
| 2018/0339017 A1* | 11/2018 | Palani | A61P 1/16 |

FOREIGN PATENT DOCUMENTS

| | | |
|---|---|---|
| CN | 1468258 A | 1/2004 |
| CN | 1918177 A | 2/2007 |
| CN | 101891823 A | 11/2010 |
| CN | 101985470 A | 3/2011 |
| CN | 1786031 B | 5/2011 |
| CN | 101337989 B | 10/2012 |
| CN | 102766204 A | 11/2012 |
| CN | 109280083 A | 1/2019 |
| WO | WO-2004005342 A1 | 1/2004 |
| WO | WO-2006074600 A1 | 7/2006 |

OTHER PUBLICATIONS

Manandhar et al., J. Med. Chem. 58:1020-1037(2015) (Year: 2015).*
Gallwitz et al., Eur. J. Biochem. 225:1151-1156 (1994) (Year: 1994).*
Fortin et al., PLoS ONE 6:e24693 (13 pages) (2011) (Year: 2011).*
Heinrich et al., J. Biol. Chem. 259:14082-14087 (1984) (Year: 1984).*
Gupta, Ind. J. Endocrinol. Metabol. 17:413-421 (2013) (Year: 2013).*
Shakesby et al., Insect Biochem. Molec. Biol. 39:1-10 (2009) (Year: 2009).*
International Search Report and Written Opinion for Application No. PCT/CN2018/112789, dated Jul. 26, 2019.
Burcelin, R. et al., "Long-Lasting Antidiabetic Effect of a Dipeptidyl Peptidase IV-Resistant Analog of Glucagon-Like Peptide-1.", *Metabolism*, vol. 48, No. 2, pp. 252-258 (1999).
Lorenz et al, "Recent progress and future options in the development of GLP-1 receptor agonists for the treatment of diabesity", *Bioorganic & Medicinal Chemistry Letters*, vol. 23, pp. 4011-4018 (2013).
Manandhar et al., "Glucagon-like Peptide-1 (GLP-1) Analogs: Recent Advances, New Possibilities, and Therapeutic Implications", *Journal of Medicinal Chemistry*, vol. 58, pp. 1020-1037 (2015).

* cited by examiner

*Primary Examiner* — Thea D' Ambrosio
(74) *Attorney, Agent, or Firm* — Marshall, Gerstein & Borun LLP

(57) ABSTRACT

The present application belongs to the field of medicine. The present application relates to a GLP-1 polypeptide having GLP-1 receptor agonist activity and the use thereof. The present application further relates to a pharmaceutical composition comprising the GLP-1 polypeptide. In particular, the present application relates to a GLP-1 polypeptide having GLP-1 receptor agonist activity, or a pharmaceutically acceptable salt thereof, characterized in that the GLP-1 polypeptide has a mutation from threonine to proline at the position corresponding to the 13th position of the amino acid sequence of GLP-1.

8 Claims, No Drawings

Specification includes a Sequence Listing.

SEQUENCE LISTING

```
<160> NUMBER OF SEQ ID NOS: 6

<210> SEQ ID NO 1
<211> LENGTH: 31
<212> TYPE: PRT
<213> ORGANISM: Artificial Sequence
<220> FEATURE:
<223> OTHER INFORMATION: Synthetic Polypeptide

<400> SEQUENCE: 1

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 2
<211> LENGTH: 30
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (30)..(30)
<223> OTHER INFORMATION: NH2

<400> SEQUENCE: 2

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 3
<211> LENGTH: 39
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (39)..(39)
<223> OTHER INFORMATION: NH2

<400> SEQUENCE: 3

His Gly Glu Gly Thr Phe Thr Ser Asp Leu Ser Lys Gln Met Glu Glu
1               5                   10                  15
```

```
Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 4
<211> LENGTH: 30
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (30)..(30)
<223> OTHER INFORMATION: NH2

<400> SEQUENCE: 4

His Gly Glu Gly Thr Phe Pro Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 5
<211> LENGTH: 31
<212> TYPE: PRT
<213> ORGANISM: Artificial Sequence
<220> FEATURE:
<223> OTHER INFORMATION: Synthetic Polypeptide

<400> SEQUENCE: 5

His Gly Glu Gly Thr Phe Pro Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 6
<211> LENGTH: 37
<212> TYPE: PRT
<213> ORGANISM: Artificial Sequence
<220> FEATURE:
<223> OTHER INFORMATION: Synthetic Polypeptide

<400> SEQUENCE: 6

His Asp Glu Phe Glu Arg His Ala Glu Gly Thr Phe Thr Ser Asp Val
1               5                   10                  15

Ser Ser Tyr Leu Glu Gly Gln Ala Ala Lys Glu Phe Ile Ala Trp Leu
            20                  25                  30

Val Lys Gly Arg Gly
        35
```

GLP-1 POLYPEPTIDE HAVING GLP-1 RECEPTOR AGONIST ACTIVITY AND USE THEREOF

INCORPORATION BY REFERENCE OF MATERIAL SUBMITTED ELECTRONICALLY

This application contains, as a separate part of disclosure, a sequence listing in computer-readable form (filename: 53861_Seqlisting.txt; 2,851 bytes; created Jan. 4, 2019) which is incorporated by reference in its entirety.

TECHNICAL FIELD

The present application belongs to the field of medicine. The present application relates to a GLP-1 polypeptide having GLP-1 receptor agonist activity and the use thereof.
The present application further relates to a pharmaceutical composition comprising the GLP-1 polypeptide.

BACKGROUND

Glucagon-like peptide-1 (GLP-1) is a polypeptide containing 37 amino acids. The amino acid sequence of GLP-1 (also referred to herein as GLP-1(1-37)) is $^1$HDEFERHAE-GTFTSDVSSYLEGQAAKEFIAWLVKGRG (SEQ ID No. 6). GLP-1 stimulates insulin secretion by agonizing the GLP-1 receptor, so as to cause a decrease in blood glucose levels (Bioorganic & Medicinal Chemistry Letters, 2013, 23, 4011-4018; J. Med. Chem., 2015, 58, 1020-1037). However, the activity of GLP-1(1-37) is very weak. Therefore, attention has been focused on derivatives of GLP-1(1-37), such as GLP-1 fragments which are stronger than GLP-1(1-37) in terms of bioactivity. Examples of GLP-1 fragments include GLP-1(7-37) and GLP-1(7-36)NH$_2$. The sequence of GLP-1(7-37) is $^7$HAEGTFTSDVS-SYLEGQAAKEFIAWLVKGRG (SEQ ID No. 1). The sequence of GLP-1(7-36)NH$_2$ is $^7$HAEGTFTSDVS-SYLEGQAAKEFIAWLVKGR-NH$_2$ (SEQ ID No. 2).

It has been found that GLP-1 has a glucose concentration-dependent blood-glucose lowering effect. In the case of patients with elevated blood glucose levels, GLP-1 functions to lower the blood glucose levels. GLP-1 would not further lower blood glucose levels in patients when their blood glucose levels are normal. Thus, GLP-1 reduces the risk of hypoglycemia that is common when administering a blood-glucose lowering medicament, so as to increase the medication safety.

GLP-1 further has the effect of losing body weight. Studies have shown that patients with type 2 diabetes have an average weight loss of 1.9 kg after 6 weeks of GLP-1 treatment. The researchers believe that GLP-1 achieves weight loss through a variety of ways, including inhibition of gastric motility, delaying gastric emptying and so on. In addition, GLP-1 can further act on the central nervous system, causing a feeling of fullness in the human body and causing a loss of appetite.

Therefore, GLP-1 has shown a great potential as a therapeutic agent for treating diabetes (especially type 2 diabetes), obesity and related conditions.

Novo Nordisk developed a GLP-1 analogue by attaching glutamic acid to lysine at the 20th position of GLP-1 and further linking hexadecanoyl (palmitoyl) to the amino group of glutamic acid, which is marketed under the trade name Liraglutide. Exenatide (also known as Exendin-4) is a natural GLP-1 analogue. Exenatide is a 39 amino acids-containing polypeptide isolated from the saliva of Helioderma suspectum. The sequence of Exenatide is HGEGTFTSDLSKQMEEEAVRLFIEW-LKNGGPSSGAPPPS-NH$_2$ (SEQ ID No. 3).

Furthermore, the 8-position alanine of GLP-1 (Ala$^8$/A$^8$) is known to be a target of dipeptidyl peptidase IV (DPP-IV). Variants obtained by replacing the 8-position alanine of GLP-1 or a fragment thereof with glycine (Gly/G), serine (Ser/S) or threonine (Thr/T) (for example, Gly$^8$-GLP-1, Ser$^8$-GLP-1 or Thr$^8$-GLP-1; see Metabolism, 1999, 48, 252-258, or Diabetologia, 1998, 41, 271-278) have increased resistance to DPP-IV mediated degradation.

SUMMARY OF THE INVENTION

The present application provides a GLP-1 polypeptide having GLP-1 receptor agonist activity, or a pharmaceutically acceptable salt thereof, characterized in that the GLP-1 polypeptide has a mutation from threonine to proline at the position corresponding to the 13th position of the amino acid sequence of GLP-1. The GLP-1 polypeptide or a pharmaceutically acceptable salt thereof described herein is a GLP-1 receptor agonist useful for treating diseases in which it is desired to activate or agonize the GLP-1 receptor.

The present application further provides the use of the GLP-1 polypeptide or a pharmaceutically acceptable salt thereof in the manufacture of a medicament for the treatment of a disease in need of activating or agonizing the GLP-1 receptor. The present application further provides a GLP-1 polypeptide or a pharmaceutically acceptable salt thereof, for use in the treatment of a disease in need of activating or agonizing the GLP-1 receptor. The present application further provides a method of treating a disease in need of activating or agonizing the GLP-1 receptor, comprising administering to a subject in need thereof a therapeutically effective amount of the GLP-1 polypeptide or a pharmaceutically acceptable salt thereof.

The present application further provides a pharmaceutical composition comprising the GLP-1 polypeptide or a pharmaceutically acceptable salt thereof, and optionally a pharmaceutically acceptable carrier.

DETAILED DESCRIPTION OF THE INVENTION

The present application provides a GLP-1 polypeptide having GLP-1 receptor agonist activity, or a pharmaceutically acceptable salt thereof, characterized in that the GLP-1 polypeptide has a mutation from threonine to proline at the position corresponding to the 13th position of the amino acid sequence of GLP-1.

In one embodiment, the GLP-1 polypeptide of the present application comprises GLP-1 having a mutation from threonine to proline at the position corresponding to the 13th position of the amino acid sequence of GLP-1; a GLP-1 fragment having a mutation from threonine to proline at the position corresponding to the 13th position of the amino acid sequence of GLP-1 and having GLP-1 receptor agonist activity; an extended GLP-1 having a mutation from threonine to proline at the position corresponding to the 13th position of the amino acid sequence of GLP-1 and having GLP-1 receptor agonist activity; or a GLP-1 analog or a fragment thereof having a mutation from threonine to proline at the position corresponding to the 13th position of the amino acid sequence of GLP-1 and having GLP-1 receptor agonist activity. The GLP-1 analogue or a fragment thereof comprises a natural analog of GLP-1 or a fragment thereof, or a GLP-1 analogue or a fragment thereof having 1, 2, 3, 4 or 5 different amino acids in its amino acid sequence from the amino acid (s) at the corresponding position in GLP-1.

In a preferred embodiment, the GLP-1 is GLP-1(1-37). In another preferred embodiment the GLP-1 fragment comprises GLP-1(7-37) or GLP-1(7-36)NH$_2$. In a preferred embodiment, the GLP-1 analogue or a fragment thereof comprises Exenatide, Gly$^8$-GLP-1(7-37), Gly$^8$-GLP-1(7-36)NH$_2$, Ser$^8$-GLP-1(7-37), Ser$^8$-GLP-1(7-36)NH$_2$, Thr$^8$-GLP-1(7-37) or Thr$^8$-GLP-1(7-36)NH$_2$.

In a preferred embodiment, the GLP-1 polypeptide described herein is Gly$^8$-Pro$^{13}$-GLP-1(7-37), Gly$^8$-Pro$^{13}$-GLP-1(7-36)NH$_2$, Ser$^8$-Pro$^{13}$-GLP-1(7-37), Ser$^8$-Pro$^{13}$-GLP-1(7-36)NH$_2$, Thr$^8$-Pro$^{13}$-GLP-1(7-37) or Thr$^8$-Pro$^{13}$-GLP-1(7-36)NH$_2$.

The sequence of Gly$^8$-Pro$^{13}$-GLP-1(7-36)NH$_2$ is (SEQ ID No. 4)
$^7$HGEGTFPSDVSSYLEGQAAKEFIAWLVKGR-NH$_2$.

The sequence of Gly$^8$-Pro$^{13}$-GLP-1(7-37) is (SEQ ID No. 5)
$^7$HGEGTFPSDVSSYLEGQAAKEFIAWLVKGRG.

Amino acids in the GLP-1 polypeptide described herein may be substituted or unsubstituted. Alternatively, amino acids in the GLP-1 polypeptide described herein may be natural amino acids or unnatural amino acids. Examples of unnatural amino acids include α-methyl amino acids (such as α-methylalanine), D-amino acids, histidine-like amino acids (such as 2-aminohistidine, β-hydroxy-histidine, homohistidine, α-fluoromethylhistidine or α-methylhistidine), amino acids containing an additional methylene group in the side chain ("homo" amino acid), and amino acids in which a carboxylic acid functional group in a a side chain is replaced by a sulfonic acid group (such as cysteine). However, unless otherwise stated, the GLP-1 polypeptide described herein preferably comprises only natural amino acids.

The GLP-1 polypeptide of the present application or a pharmaceutically acceptable salt thereof can be prepared using a known method in the art, such as solid phase peptide synthesis technology (see CN101337989B, and CN1786031B). Peptide synthesizers are commercially available from, for example, Applied Biosystems. Reagents for solid phase synthesis are commercially available from, for example, Midwest Biotech or GL Biochem. The solid phase peptide synthesizer can be used to block interfering groups, protect amino acids to be reacted, couple, decouple, and cap unreacted amino acids according to the manufacturer's instructions. The GLP-1 polypeptide of the present application or a pharmaceutically acceptable salt thereof can also be prepared by a genetic engineering method.

The numbering of amino acids in the GLP-1 polypeptide, GLP-1, GLP-1 fragment, extended GLP-1, GLP-1 analog or a fragment thereof described herein is determined in a manner generally accepted in the art (e.g., determined according to the numbering of the amino acid sequence of GLP-1). For example, according to the practice in the art, the amino terminus of GLP-1 (7-37) is designated as position 7, and the carboxy terminus is designated as position 37. The other amino acids in the polypeptide are numbered sequentially. The C-terminus is an unsubstituted carboxy form, unless otherwise specified.

Definition

In some embodiments, GLP-1 refers to GLP-1 (1-37) having 37 amino acids. In still other embodiments, GLP-1 refers to GLP-1, a GLP-1 fragment, an extended GLP-1, a GLP-1 analog, or a fragment thereof. Those skilled in the art are able to determine the meaning of the term GLP-1 based on the context.

"GLP-1 polypeptide" includes GLP-1 having a mutation from threonine to proline at the position corresponding to the 13th position of the amino acid sequence of GLP-1 (i.e., a T13P mutation); a GLP-1 fragment having a mutation from threonine to proline at the position corresponding to the 13th position of the amino acid sequence of GLP-1 and having GLP-1 receptor agonist activity; an extended GLP-1 having a mutation from threonine to proline at the position corresponding to the 13th position of the amino acid sequence of GLP-1 and having GLP-1 receptor agonist activity; or a GLP-1 analog or a fragment thereof having a mutation from threonine to proline at the position corresponding to the 13th position of the amino acid sequence of GLP-1 and having GLP-1 receptor agonist activity.

"GLP-1" is GLP-1(1-37).

"GLP-1 fragment" is a fragment of GLP-1 having GLP-1 receptor agonist activity (for example, GLP-1(7-37), GLP-1(7-36)NH$_2$). The GLP-1 fragment includes a polypeptide obtained by truncating one or more amino acids at the N-terminus or C-terminus of GLP-1 or a fragment thereof (for example, GLP-1(1-37), GLP-1(7-37), GLP-1(7-36)NH$_2$). For example, GLP-1(9-36) represents a fragment obtained by truncating 2 amino acids at the N-terminus and 1 amino acid at the C-terminus of GLP-1(7-37). Moreover, the amino acids in the fragment are numbered with the same number as the corresponding amino acid number in GLP-1(7-37). For example, the N-terminal glutamic acid in GLP-1(9-36) is at the 9th position; the 12th position is phenylalanine, and the 22nd position is glycine, which is the same as GLP-1(7-37). Preferably, the amino acids in the GLP-1 fragment are numbered with the same number as the corresponding amino acid number in GLP-1.

"Extended GLP-1" refers to a polypeptide having GLP-1 receptor agonist activity obtained by adding one or more amino acids to the N-terminus and/or C-terminus of GLP-1 or a fragment thereof (for example, GLP-1(1-37), GLP-1(7-37), GLP-1(7-36)NH$_2$). For example, GLP-1(5-37) can be obtained by adding two amino acids at the N-terminus of GLP-1(7-37); and GLP-1(7-38) can be obtained by adding one amino acid at the C-terminus of GLP-1(7-37). Preferably, the amino acids in the extended GLP-1 are numbered with the same number as the corresponding amino acid number in GLP-1 or a fragment thereof (for example, GLP-1(1-37), GLP-1(7-37), GLP-1(7-36)NH$_2$).

"GLP-1 analogue or a fragment thereof" refers to a polypeptide having homology to GLP-1 or a fragment thereof (for example, GLP-1(1-37), GLP-1(7-37), GLP-1(7-36)NH$_2$) and also having GLP-1 receptor agonist activity. The GLP-1 analogue or a fragment thereof comprises a natural analog of GLP-1 or a fragment thereof, or a GLP-1 analogue or a fragment thereof having 1, 2, 3, 4 or 5 different amino acids in its amino acid sequence from the amino acid(s) at the corresponding position in GLP-1. In a preferred embodiment, the GLP-1 analogue or a fragment thereof comprises Exenatide, Gly$^8$-GLP-1(1-37), Gly$^8$-GLP-1(7-36)NH$_2$, Ser$^8$-GLP-1(7-37), Ser$^8$-GLP-1(7-36)NH$_2$, Thr$^8$-GLP-1(1-37) or Thr$^8$-GLP-1(7-36)NH$_2$. Preferably, the amino acids in the GLP-1 analogue or a fragment thereof are numbered with the same number as the corresponding amino acid number in GLP-1 or a fragment thereof (for example, GLP-1(1-37), GLP-1(7-37), GLP-1(7-36)NH$_2$).

In a preferred embodiment, the GLP-1 polypeptide described herein is Gly$^8$-Pro$^{13}$-GLP-1(7-37), Gly$^8$-Pro$^{13}$-GLP-1(7-36)NH$_2$, Ser$^8$-Pro$^{13}$-GLP-1(7-37), Ser$^8$-Pro$^{13}$-GLP-1(7-36)NH$_2$, Thr$^8$-Pro$^{13}$-GLP-1(7-37) or Thr$^8$-Pro$^{13}$-GLP-1(7-36)NH$_2$.

In one embodiment, the N-terminus of the GLP-1 polypeptide described herein is unsubstituted. In another embodiment, the N-terminus of the GLP-1 polypeptide described herein is alkylated or acylated (preferably alkylated or acylated by using a $C_1$-$C_{20}$ alkyl or acyl group). In one embodiment, the C-terminus of the GLP-1 polypeptide described herein is unsubstituted. In another embodiment, the C-terminus of the GLP-1 polypeptide described herein is amidated with a —NH$_2$, —NHR or —NRR' group or esterified with a ($C_1$-$C_{20}$) alkyl group.

Since the GLP-1 polypeptides described herein may contain an acidic, a basic functional group or both in its amino acid sequence, the GLP-1 polypeptides described herein are capable of reacting with a variety of inorganic bases, inorganic acids, and organic acids to form salts. The acids commonly used to form acidic salts are inorganic acids such as hydrochloric acid, hydrobromic acid, hydroiodic acid, sulfuric acid, phosphoric acid, etc., and organic acids such as p-toluenesulfonic acid, methanesulfonic acid, oxalic acid, p-bromobenzenesulfonic acid, carbonic acid, succinic acid, citric acid, benzoic acid, acetic acid, and the like. Examples of such salts include sulfate, pyrosulfate, hydrogen sulfate, sulfite, bisulfite, phosphates, monohydrogen phosphate, dihydrogen phosphate, metaphosphate, pyrophosphate, chloride, bromine, iodide, acetate, propionate, caprate, octoate, acrylate, formate, isobutyrate, hexanoate, heptanoate, propiolate, oxalate, malonate, succinate, suberate, sebacate, fumarate, maleate, butene-1,4-diate, hexene-1,6-diate, benzoate, chlorobenzoate, methyl benzoate, dinitrobenzoate, hydroxybenzoate, methoxybenzoate, phthalate, tartrate, methanesulfonate, propanesulfonate, naphthalene-1-sulfonate, naphthalene-2-sulfonate, mandelate, and the like.

The base addition salt can be formed from an inorganic base such as ammonium, an alkali metal or alkaline earth metal hydroxide, a carbonate, a bicarbonate or the like. The following basic substances are commonly used to form basic salts, for example, sodium hydroxide, potassium hydroxide, ammonium hydroxide, potassium carbonate and the like. Preferably, the salt of the GLP-1 polypeptide described herein is a pharmaceutically acceptable salt.

Diseases in need of activating or agonizing the GLP-1 receptor as described herein include one or more diseases selected from the group consisting of diabetes (e.g., type 1 diabetes or type 2 diabetes), obesity, stroke, catabolic changes after surgery, or irritable bowel syndrome.

The present application further provides the use of the GLP-1 polypeptide or a pharmaceutically acceptable salt thereof in the manufacture of a medicament for the treatment of a disease in need of activating or agonizing the GLP-1 receptor. The present application further provides a GLP-1 polypeptide or a pharmaceutically acceptable salt thereof, for use in the treatment of a disease in need of activating or agonizing the GLP-1 receptor. The present application further provides a method of treating a disease in need of activating or agonizing the GLP-1 receptor, comprising administering to a subject in need thereof a therapeutically effective amount of the GLP-1 polypeptide or a pharmaceutically acceptable salt thereof.

The present application further provides a pharmaceutical composition comprising the GLP-1 polypeptide or a pharmaceutically acceptable salt thereof, and optionally a pharmaceutically acceptable carrier. The pharmaceutical composition described herein may be a tablet, a capsule, a granule, a syrup, a suspension, a solution, a dispersion, a slow release preparation for oral or non-oral administration, an intravenous injection preparation, a subcutaneous injection preparation, an inhalation preparation, a transdermal preparation, a rectal or vaginal suppository.

The pharmaceutically acceptable carrier described herein refers to a pharmaceutically acceptable carrier well known to those skilled in the art, and the pharmaceutically acceptable carrier of the present application includes, but is not limited to, a filler, a wetting agent, a binder, a disintegrating agent, a lubricant, a binder, a glidant, a flavoring agent, a surfactant, a preservative, and the like. Fillers include, but are not limited to, lactose, microcrystalline cellulose, starch, powdered sugar, dextrin, mannitol, calcium sulfate, and the like. Wetting agents and binders include, but are not limited to, sodium carboxymethylcellulose, hydroxypropylcellulose, hydroxypropyl methyl cellulose, gelatin, sucrose, polyvinylpyrrolidone, and the like. Disintegrating agents include, but are not limited to, sodium carboxymethyl starch, crosslinked polyvinylpyrrolidone, croscarmellose sodium, low substituted hydroxypropylcellulose, and the like. Lubricants include, but are not limited to, magnesium stearate, aerosil, talc, hydrogenated vegetable oil, polyethylene glycol, magnesium lauryl sulfate, and the like. Binders include, but are not limited to, gum arabic, alginic acid, calcium carboxymethylcellulose, sodium carboxymethylcellulose, glucose, dextrin, dextrose, ethylcellulose, gelatin, liquid glucose, guar gum, hydroxyethyl cellulose, hydroxypropyl cellulose, hydroxypropyl methyl cellulose, magnesium aluminum silicate, maltodextrin, methyl cellulose, polymethacrylate, polyvinylpyrrolidone, pregelatinized starch, sodium alginate, sorbitol, starch, syrup and tragacanth. Glidants include, but are not limited to, colloidal silica, powdered cellulose, magnesium trisilicate, silica, and talc. Flavoring agents include, but are not limited to, aspartame, stevioside, fructose, glucose, syrup, honey, xylitol, mannitol, lactose, sorbitol, maltitol, glycyrrhizin. Surfactants include, but are not limited to, Tween-80, poloxamer. Preservatives include, but are not limited to, paraben, sodium benzoate, potassium sorbate, and the like.

Methods of preparing various pharmaceutical compositions containing various amounts of active ingredients are known, or will be apparent to those skilled in the art in light of this disclosure, as described in REMINGTON'S PHARMACEUTICAL SCIENCES, Martin, E. W., ed., Mack Publishing Company, 19th ed. (1995). Methods of preparing the pharmaceutical compositions include incorporation of suitable pharmaceutical excipients, carriers, diluents and the like. The pharmaceutical compositions described herein are made in a known manner, including conventional methods of mixing, dissolving or lyophilizing.

In the pharmaceutical compositions described herein, the amount of active ingredient may vary from about 0.01% to about 99% by weight of a given unit dosage form. In such therapeutically useful pharmaceutical composition formulations, the active ingredient is in an amount such that an effective dosage level can be obtained.

The tablet, capsule and the like described herein may comprise: a binder such as tragacanth, gum arabic, corn starch or gelatin; an excipient such as dicalcium phosphate; a disintegrating agent such as corn starch, potato starch, alginic acid, etc.; a lubricant such as magnesium stearate;

and a sweetener such as sucrose, fructose, lactose or aspartame; or a flavoring agent such as mint, wintergreen or cherry flavor. When the unit dosage form is a capsule, it may contain, in addition to materials of the above types, a liquid carrier such as vegetable oil or polyethylene glycol. Various other materials may be present, as a coating, or otherwise alter the physical form of the solid unit dosage form. For example, tablets or capsules may be coated with gelatin, wax, shellac or sugar, etc. The syrup may contain an active ingredient, sucrose or fructose as a sweetener, methylparaben or propylparaben as a preservative, a dye and a flavoring agent such as cherry or orange flavor. Of course, any material used to prepare any unit dosage form should be pharmaceutically acceptable and non-toxic in the amounts employed. In addition, the active ingredient can be incorporated into a slow release formulations and a slow release device.

The active ingredient can also be administered intravenously or intraperitoneally by infusion or injection. An aqueous solution of the active ingredient or a salt thereof can be prepared, optionally with a non-toxic surfactant. Dispersions in glycerol, liquid polyethylene glycol, triacetin and mixtures thereof, and oils can also be prepared. Under ordinary conditions of storage and use, these formulations contain a preservative to prevent the growth of microorganisms.

Pharmaceutical composition dosage forms suitable for injection or infusion may comprise sterile aqueous solution or dispersion or sterile powder comprising an active ingredient suitable for the ready-to-use preparation of a sterile, injectable or infusible solution or dispersion (optionally encapsulated in a liposome). In all cases, the final dosage forms must be sterile, liquid, and stable under the conditions of manufacture and storage. The liquid carrier may be a solvent or liquid dispersion medium including, for example, water, ethanol, polyols (for example, glycerol, propylene glycol, liquid polyethylene glycol, and the like), vegetable oils, non-toxic glycerides, and suitable mixtures thereof. Proper fluidity can be maintained, for example, by liposome formation, by maintaining the desired particle size in the case of dispersion, or by the use of a surfactant. The prevention of microorganisms can be achieved by using various antibacterial and antifungal agents such as parabens, chlorobutanol, phenol, sorbic acid, thimerosal, and the like. In many cases, it will be preferred to include isotonic agents, such as sugars, buffers or sodium chloride. Prolonged absorption of the injectable composition can be brought about by the use of a composition that comprises an absorption delaying agent (for example, aluminum monostearate and gelatin).

Sterile injectable solutions are prepared by combining the active ingredient in a desired amount in a suitable solvent with the various other ingredients listed above, followed by filter sterilization. In the case of sterile powders for the preparation of sterile injectable solutions, the preferred preparation methods are vacuum drying and lyophilization techniques which result in powders of the active ingredient plus any additionally desired ingredients present in the sterile filtration solution.

Useful solid carriers include comminuted solids (e.g., talc, clay, microcrystalline cellulose, silica, alumina, etc.). Useful liquid carriers include water, ethanol or ethylene glycol or a water-ethanol/ethylene glycol mixture, and the pharmaceutical compositions of the present application may be dissolved or dispersed in the liquid carriers in an effective amount, optionally with the aid of a non-toxic surfactant. Adjuvants (such as fragrances) and additional antimicrobial agents can be added to optimize the properties for a given use.

Thickeners (such as synthetic polymers, fatty acids, fatty acid salts and esters, fatty alcohols, modified celluloses or modified inorganic materials) can also be used with liquid carriers to form coatable pastes, gels, ointments, soaps, etc. that are used directly on the user's skin.

The therapeutically effective amount of the active ingredient will depend not only on the particular salt selected, but also on the administration route, the property of the disease to be treated, and the age and conditions of the patient, and will ultimately depend on the decision of the attending physician or clinician.

The above formulations may be presented in unit dosage form, which is a physically discrete unit containing a unit dose suitable for administration to humans and other mammalian bodies. The unit dosage form may be a capsule or a tablet. The amount of active ingredient in the unit dose may vary or be adjusted between about 0.01 to about 1000 mg or more, depending on the particular treatment involved.

The term "treated", "treating" or "treatment" as used herein generally refers to the acquisition of the desired pharmacological and/or physiological effect. The effect may be prophylactic according to the prevention of the disease or its symptoms in whole or in part; and/or may be therapeutic according to the partial or complete stabilization or cure of the disease and/or the side effect due to the disease. As used herein, "treated", "treating" or "treatment" encompasses any treatment for the disease of a patient, including: (a) prevention of the disease or condition in the patient that may be predisposed to the disease or condition but has not yet been diagnosed; (b) inhibition of the symptoms of the disease, i.e., preventing its development; or (c) remission of the symptoms of the disease, i.e., causing regression of the disease or symptoms in whole or in part.

The GLP-1 polypeptide described herein, or a pharmaceutically acceptable salt thereof, may also be administered in combination with one or more additional therapeutic agents for the treatment of diabetes. Such additional therapeutic agents include, but are not limited to, sulfonylureas (e.g., glibenclamide, gliclazide, glipizide, gliquidone, glimepiride, etc.), biguanides (e.g., metformin)), α-glucosidase inhibitors (acarbose, voglibose, etc.), thiazolidinediones (e.g., rosiglitazone).

EXAMPLES

Hereinafter, the present application will demonstrate the beneficial effects of the present application by way of examples. Those skilled in the art will recognize that these examples are illustrative and not restrictive. These examples will do not limit the scope of the present application in any way. The experimental methods described in the following examples, unless otherwise specified, are conventional methods; the reagents and materials, unless otherwise specified, are commercially available.

Example 1: Preparation of $Gly^8$-$Pro^{13}$-GLP-1(7-36)$NH_2$

The primary structure of $Gly^8$-$Pro^{13}$-GLP-1(7-36)$NH_2$ is: His-Gly-Glu-Gly-Thr-Phe-Pro-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-$NH_2$ (SEQ ID No. 4). In this example, MBHA Rink amide resin (purchased from GL Biochem) was used to synthesize $Gly^8$-$Pro^{13}$-GLP-1(7-36)$NH_2$ in the sequence from Arg to His.

1.1) Coupling of the First Amino Acid Fmoc-Arg(Pbf)-OH with MBHA Rink Amide Resin:

100 g of MBHA Rink amide resin was added to a 2 L reaction flask, followed by the addition of 1 L of 25% hexahydropyridine/DMF solution to the reaction flask. After 30 minutes, the hexahydropyridine/DMF solution was removed by a negative pressure suction device. Then, 32.7 g of Fmoc-Arg(Pbf)-OH, 6.8 g of 1-hydroxybenzotriazole (HOBt), 7.84 ml of N,N-diisopropylcarbodiimide (DIC) and 500 ml of DMF were added to the reaction flask. The reaction was continued for 120 minutes. The resin was collected by filtration. The collected resin was washed successively with isopropyl alcohol, DMF, isopropyl alcohol, DMF, isopropyl alcohol, and diethyl ether. The washed resin was dried to constant weight.

1.2) Coupling of the Second Amino Acid:

1.2.1) Deprotection: The dried resin with the first amino acid was added to a 2 L reaction flask. To the reaction flask was added 1 L of DMF to sufficiently swell the resin. The DMF is moved into a bottle for stroring waste liquid via a negative pressure suction device. 1 L of 25% hexahydropyridine/DMF solution was added to the reaction flask, and then the reaction flask was placed on a shaker (shaker speed: 120 rpm) for 30 minutes. The liquid was moved into a bottle for stroring waste liquid via a negative pressure suction device. The resin was washed successively with DMF, isopropyl alcohol, DMF, isopropanol, DMF, and the washing liquid was transferred to a bottle for stroring waste liquid via a negative pressure suction device after each washing.

1.2.2) Coupling reaction: 53.5 g of Fmoc-Gly-OH, 28.0 ml of DIC and 24.3 g of HOBt were placed in an Erlenmeyer flask, and then dissolved by adding 500 ml of DMF to obtain a solution. The Erlenmeyer flask was placed on a shaker for activation for 10 minutes (shaker speed: 120 rpm) to obtain an activated solution. The activated solution was added to the reaction flask containing the resin obtained in step 1.2.1). The reaction flask was then placed in a shaker (shaker speed: 120 rpm) for 120 minutes. The liquid was moved into a bottle for stroring waste liquid via a negative pressure suction device. The resin was washed successively with DMF, isopropyl alcohol, DMF, and isopropyl alcohol, and the washing liquid was transferred to a bottle for stroring waste liquid via a negative pressure suction device after each washing. The washed resin was dried to constant weight.

1.3) Coupling of the 3rd to 30th Amino Acids:

Step 1.2) was repeated using 84.3 g of Fmoc-Lys(Boc)-OH, 61.1 g of Fmoc-Val-OH, 63.6 g of Fmoc-Leu-OH, 94.8 g of Fmoc-Trp(BOC)-OH, 56.0 g of Fmoc-Ala-OH, 63.6 g of Fmoc-Ile-OH, 69.7 g Fmoc-Phe-OH, 76.6 g Fmoc-Glu(O$^t$Bu)-OH, 84.3 g of Fmoc-Lys(Boc)-OH, 56.0 g of Fmoc-Ala-OH, 56.0 g of Fmoc-Ala-OH, 109.9 g of Fmoc-Gln(Trt)-OH, 53.5 g of Fmoc-Gly-OH, 76.6 g of Fmoc-Glu(O$^t$Bu)-OH, 63.6 g of Fmoc-Leu-OH, 82.7 g of Fmoc-Tyr($^t$Bu)-OH 69.0 g of Fmoc-Ser($^t$Bu)-OH, 69.0 g of Fmoc-Ser($^t$Bu)-OH, 61.1 g of Fmoc-Val-OH, 74.07 g of Fmoc-Asp(O$^t$Bu)-OH, 69.0 g of Fmoc-Ser($^t$Bu)-OH, 60.7 g of Fmoc-Pro-OH, 69.7 g of Fmoc-Phe-OH, 71.5 g of Fmoc-Thr($^t$Bu)-OH, 53.5 g of Fmoc-Gly-OH, 109.9 g of Fmoc-Glu(O$^t$Bu)-OH, 53.5 g of Fmoc-Gly-OH, and 111.5 g of Fmoc-His(Trt)-OH as reaction reagents in sequence to obtain dried His(Trt)-Gly-Glu(O$^t$Bu)-Gly-Thr($^t$Bu)-Phe-Pro-Ser($^t$Bu)-Asp(O$^t$Bu)-Val-Ser($^t$Bu)-Ser($^t$Bu)-Tyr(tBu)-Leu-Glu(O$^t$Bu)-Gly-Gln(Trt)-Ala-Ala-Lys(Boc)-Glu(O$^t$Bu)-Phe-Ile-Ala-Trp(Boc)-Leu-Val-Lys(Boc)-Gly-Arg(pbf)-resin (SEQ ID No. 4).

1.4) The dried His(Trt)-Gly-Glu(O$^t$Bu)-Gly-Thr($^t$Bu)-Phe-Pro-Ser($^t$Bu)-Asp(O$^t$Bu)-Val-Ser($^t$Bu)-Ser($^t$Bu)-Tyr($^t$Bu)-Leu-Glu(O$^t$Bu)-Gly-Gln(Trt)-Ala-Ala-Lys(Boc)-Glu(O$^t$Bu)-Phe-Ile-Ala-Trp(Boc)-Leu-Val-Lys(Boc)-Gly-Arg(pbf)-resin (SEQ ID No. 4) was added to a 2 L round bottom flask. 1 L of TFA/$H_2O$/EDT (V/V/V=95:2.5:2.5) was added to the flask. The flask was placed on a shaker for 2 hours (120 rpm). The reaction liquid was filtered to obtain a filtrate. The filtrate was added portionwise to 3 L of anhydrous diethyl ether to give a white precipitate. The precipitate was collected by filtration and weighed, and 220 g of crude $Gly^8$-$Pro^{13}$-GLP-1(7-36)$NH_2$ was obtained. The crude product was purified by HPLC to give purified $Gly^8$-$Pro^{13}$-GLP-1(7-36)$NH_2$: MS m/z=3,280.6 (single charged); 1640.8 (double charged); 1094.2 (tri-charged).

Example 2: Efficacy Study of $Gly^8$-$Pro^{13}$-GLP-1(7-36)$NH_2$, Exenatide and Liraglutide by Way of Subcutaneous Administration 1) The Experimental Animal Model of Type 2 Diabetes Male Wistar rats of approximately 200 grams were fasted overnight with free access to water. The rats were administered a single dose of streptozotocin (STZ) by intraperitoneal injection (ip) in an amount of 45 mg/Kg. Then, the rats were normally fed and tested for fasting blood glucose. Fasting blood glucose in rats that is consistently and stably higher than 20 mM suggests a successful modeling.

2) Experimental Method

Forty-eight rats were randomly divided into 6 groups, with each of 8 rats. At the beginning of the experiment (0 hour), the blood glucose concentration of the rats (STZ rats) was 26.1±1.7 mM (n=48). At 0 hour, the STZ rats were injected subcutaneously with different doses of drugs for test. At 3, 6, and 9 hours, blood samples were taken from the vein of the rats' tail. The blood samples were tested to provide the blood glucose concentrations of the rats.

The experimental results are shown in the table below.

TABLE 1

|  | Blood glucose concentration at 0 hour (mM, mean ± sem) | Blood glucose concentration at 3 hour (mM, mean ± sem) | Blood glucose concentration at 6 hour (mM, mean ± sem) | Blood glucose concentration at 9 hour (mM, mean ± sem) |
| --- | --- | --- | --- | --- |
| $Gly^8$-$Pro^{13}$-GLP-1(7-36)$NH_2$ (1 µg/kg) | 27.4 ± 0.8 | 23.4 ± 1.1 | 19.5 ± 0.5 | 16.3 ± 0.7 |
| Liraglutide (1 µg/kg) | 24.6 ± 2.6 | 24.5 ± 2.4 | 23.0 ± 2.3 | 22.4 ± 2.5 |
| Exenatide (1 µg/kg) | 25.4 ± 1.2 | 20.6 ± 0.9 | 16.9 ± 0.6 | 12.6 ± 0.9 |

TABLE 1-continued

|  | Blood glucose concentration at 0 hour (mM, mean ± sem) | Blood glucose concentration at 3 hour (mM, mean ± sem) | Blood glucose concentration at 6 hour (mM, mean ± sem) | Blood glucose concentration at 9 hour (mM, mean ± sem) |
|---|---|---|---|---|
| Gly$^8$-Pro$^{13}$-GLP-1(7-36)NH$_2$ (10 μg/kg) | 24.0 ± 1.1 | 18.5 ± 0.9 | 14.5 ± 0.8 | 10.5 ± 0.6 |
| Liraglutide (10 μg/kg) | 23.3 ± 0.8 | 22.5 ± 0.8 | 20.8 ± 0.8 | 19.7 ± 0.6 |

The above data showed that the blood-glucose lowering effect of Gly$^8$-Pro$^{13}$-GLP-1(7-36)NH$_2$ was significantly better than that of Liraglutide ($P<0.01$).

The blood-glucose lowering effect of Gly$^8$-Pro$^{13}$-GLP-1(7-36)NH$_2$ was similar to that of Exenatide, without a significant difference between the two. However, it is expected that Gly$^8$-Pro$^{13}$-GLP-1(7-36)NH$_2$ can cause less abnormal immune responses than Exenatide.

The invention claimed is:

1. A GLP-1 polypeptide having GLP-1 receptor agonist activity, or a pharmaceutically acceptable salt thereof, characterized in that the GLP-1 polypeptide has a mutation from threonine to proline at the position corresponding to the 13th position of the amino acid sequence of GLP-1,
wherein the GLP-1 polypeptide is $Gly^8$-$Pro^{13}$-GLP-1(1-37), $Gly^8$-$Pro^{13}$-GLP-1(7-37), $Gly^8$-$Pro^{13}$-GLP-1(7-36)$NH_2$, $Ser^8$-$Pro^{13}$-GLP-1(1-37), $Ser^8$-$Pro^{13}$-GLP-1(7-37), $Ser^8$-$Pro^{13}$-GLP-1(7-36)$NH_2$, $Thr^8$-$Pro^{13}$-GLP-1(1-37), $Thr^8$-$Pro^{13}$-GLP-1(7-37) or $Thr^8$-$Pro^{13}$-GLP-1(7-36)$NH_2$.

2. The GLP-1 polypeptide or a pharmaceutically acceptable salt thereof according to claim 1, wherein the GLP-1 polypeptide is selected from the group consisting of $Gly^8$-$Pro^{13}$GLP-1(1-37), $Ser^8$-$Pro^{13}$GLP-1(1-37), and $Thr^8$-$Pro^{13}$GLP-1(1-37).

3. The GLP-1 polypeptide or a pharmaceutically acceptable salt thereof according to claim 1, wherein the GLP-1 polypeptide is selected from the group consisting of $Gly^8$-$Pro^{13}$GLP-1(7-37), $Ser^8$-$Pro^{13}$GLP-1(7-37), $Thr^8$-$Pro^{13}$GLP-1(7-37), $Gly^8$-$Pro^{13}$GLP-1(7-36)$NH_2$, $Ser^8$-$Pro^{13}$GLP-1(7-36)$NH_2$, and $Thr^8$-$Pro^{13}$GLP-1(7-36)$NH_2$.

4. The GLP-1 polypeptide or a pharmaceutically acceptable salt thereof according to claim 1, for use in the treatment of a disease in need of activating or agonizing the GLP-1 receptor.

5. A pharmaceutical composition comprising the GLP-1 polypeptide or a pharmaceutically acceptable salt thereof according to claim 1, and optionally a pharmaceutically acceptable carrier.

6. The pharmaceutical composition according to claim 5, wherein the pharmaceutical composition is a tablet, a capsule, a granule, a syrup, a suspension, a solution, a dispersion, a slow release preparation for oral or non-oral administration, an intravenous injection preparation, a subcutaneous injection preparation, an inhalation preparation, a transdermal preparation, a rectal or vaginal suppository.

7. A method of treating a disease in need of activating or agonizing the GLP-1 receptor, comprising administering to a subject in need thereof a therapeutically effective amount of the GLP-1 polypeptide or a pharmaceutically acceptable salt thereof according to claim 1.

8. The method according to claim 7, wherein the disease in need of activating or agonizing the GLP-1 receptor is selected from the group consisting of diabetes, obesity, stroke, catabolic changes after surgery, and irritable bowel syndrome.

* * * * *